United States Patent [19]

Lebreton et al.

[11] Patent Number: 5,733,928
[45] Date of Patent: Mar. 31, 1998

[54] 15-DEOXYSPERGUALIN ANALOGS, THEIR METHOD OF PREPARATION AND THEIR USE IN THERAPEUTICS

[75] Inventors: Luc Lebreton, Dijon; Patrice Renaut, Hauteville-Lès-Dijon; Christine Dumas, Versailles, all of France

[73] Assignee: Fournier Industrie et Sante, Paris, France

[21] Appl. No.: 647,813

[22] Filed: May 15, 1996

[30] Foreign Application Priority Data

May 17, 1995 [FR] France ................................ 95 05862

[51] Int. Cl.$^6$ ............................................ A61K 31/27
[52] U.S. Cl. ............................................ 514/478; 560/159
[58] Field of Search .................. 560/159; 514/476, 514/478

[56] References Cited

FOREIGN PATENT DOCUMENTS

| 0105193 | 4/1984 | European Pat. Off. |
|---------|--------|--------------------|
| 181592  | 11/1984 | European Pat. Off. |
| 0394684 | 10/1990 | European Pat. Off. |
| 0600762 | 6/1994 | European Pat. Off. |
| 0669316 | 8/1995 | European Pat. Off. |

OTHER PUBLICATIONS

R. Nishizawa et al., *The Journal of Antibiotics*, "Synthesis and Biological Activity of Spergualin Analogues" vol. XLI, No. 11, p. 1629–1643. (1988).

Yoshihisa Umeda et al., *The Journal of Antibiotics*, "Synthesis and Antitumor Activity of Spergualin Analogues", vol. XL, No. 9, pp. 1303–1315, (1987).

Yoshihisa Umeda et al., *The Journal of Antibiotics*, "Synthesis and Antitumor Activity of Spergualin Analogues I. Chemical Modification of 7-Guanidino-3-hydroxyacyl Moiety", vol. XXXVIII No. 7, pp. 886–898, (1985).

P. S. Almond et al., *Annals New York Academy of Sciences*, "Rapamycn in a Porcine Renal Transplant Model", pp. 120–201. (1993).

*Primary Examiner*—Michael L. Shippen
*Attorney, Agent, or Firm*—Ostrolenk, Faber, Gerb & Soffen, LLP

[57] ABSTRACT

The present invention relates to a novel compound selected from the group consisting of:
(i) the compounds of the formula $$H_2N-C(=NH)-NH-(CH_2)_6-CH(NH_2)-CH_2-A-NH-C(=O)-(CH_2)_4-NH-(CH_2)_2-*CH(R)-NH_2 \quad (I)$$

in which:

A is a group —CO—NH— or a group —NH—CO—,

R is a hydrogen atom or a methyl group, and

*C, if R is not the hydrogen atom, is an asymmetric carbon of (R,S) or (R) configuration; and (ii) their addition salts.

It further relates to the method of preparing this compound and to its use in therapeutics.

15 Claims, No Drawings

15-DEOXYSPERGUALIN ANALOGS, THEIR METHOD OF PREPARATION AND THEIR USE IN THERAPEUTICS

FIELD OF THE INVENTION

The present invention relates to novel compounds whose structure is related to that of 15-deoxyspergualin. It further relates to their method of preparation and to their use in therapeutics, especially as immunosuppressants.

PRIOR ART

It is known that 15-deoxyspergualin (DSG), which has the structural formula

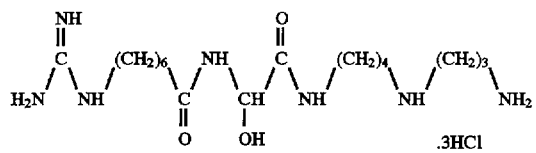

and which is also known by the international non-proprietary name "Gusperimus", possesses a valuable activity in the field of immunosuppression. Numerous publications refer to this activity: in particular, a series of articles on this subject may be found in "Immunomodulating Drugs"— Annals of the New York Academy of Sciences, vol. 685, pages 123 to 201.

However, 15-deoxyspergualin does not have a satisfactory chemical stability and attempts have been made to obtain more stable compounds, for example (i) by replacing the α-hydroxyglycine group of 15-deoxyspergualin with various α- or ω-amino acids, (ii) by modifying the structure of the central portion of the chain, or else (iii) by modifying the portion of the chain carrying the guanidine group. Examples of such modifications are described in EP-A-0 181 592, EP-A-0 105 193 and FR-A-2 698 628.

The modifications involving the hydroxyglycine residue have been reported essentially in J. Antibiot. 38, 886–898, and J. Antibiot. 41, 1629–1643. According to these publications, none of the proposed structures made it possible to obtain an activity greater than that of DSG. Likewise, the modifications made to the spermidine residue, which have been published essentially in J. Antibiot. 40, 1303–1315, have mostly led to a loss of activity and the presence of the spermidine linkage seemed to be indispensable for obtaining an active compound.

Now, it has just been found that compounds having a structure related to that of DSG but no longer comprising the hydroxyglycine linkage and the spermidine linkage nevertheless have an activity in the field of immunosuppression and that this activity can be greater than that of DSG.

SUBJECT OF THE INVENTION

The present invention proposes novel compounds whose general structure is related to that of 15-deoxyspergualin, which are chemically stable and which have a greater activity than the known products of the prior art, especially in the field of immunosuppression.

The essential difference between the compounds according to the invention and the known products of the prior art derives from a substantial modification of the central part of the molecule to give a group of the carbamate type. Furthermore, in contrast to all the known products of the prior art related to 15-deoxyspergualin, the compounds according to the invention contain a group of the amino alcohol type rather than a polyamine linkage of the spermidine type.

The compounds according to the invention are selected from the group consisting of:
(i) the compounds of the formula

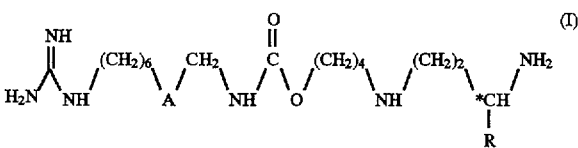

in which:

A is a group —CO—NH— or a group —NH—CO—,

R is a hydrogen atom or a methyl group, and

*C, if R is not the hydrogen atom, is an asymmetric carbon whose configuration can be undetermined (R,S) or determined (R); and (ii) their addition salts.

According to the invention, a method of preparing the compounds of formula I and their addition salts is also recommended, said method comprising the deprotection of a compound of the formula

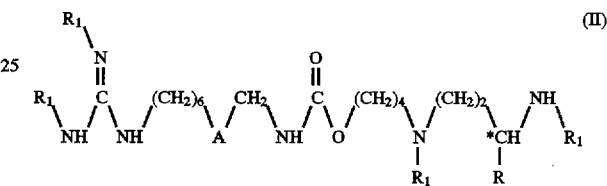

in which:

A is a group —NH—CO— or a group —CO—NH—,

R is a hydrogen atom or a methyl group,

*C, if R is not the hydrogen atom, is an asymmetric carbon of (R,S) configuration or (R) configuration, and at least one of the substituents $R_1$ is a protecting group for the amine group, the others being a hydrogen atom, by a reaction treatment known to those skilled in the art, in order to effect the deprotection of the amine groups protected by amino-protecting groups $R_1$, and the replacement of all the amino-protecting groups $R_1$ with a hydrogen atom.

The use of a substance selected from the compounds of formula I, their non-toxic addition salts and mixtures thereof is also recommended for obtaining a drug intended for use in therapeutics for the treatment or prevention of immune disorders or malaria, or for use as a pharmacological reagent.

DETAILED DESCRIPTION OF THE INVENTION

"Addition salts" are understood here as meaning the acid addition salts obtained by reacting a compound of formula I with a mineral acid or an organic acid. The preferred mineral acids for salification are hydrochloric, hydrobromic, phosphoric and sulfuric acids. The preferred organic acids for salification are fumaric, maleic, methanesulfonic, oxalic, citric and trifluoroacetic acids.

As indicated in formula I, the compounds according to the invention contain a carbon denoted by *C, which is an asymmetric carbon if R is not a hydrogen atom. When R is not a hydrogen atom, the compounds of formula I covered by the present invention include the racemic compounds, where *C has the (R,S) configuration, and the enantiomer where *C has the (R) configuration, in accordance with the rules of structural determination described by Cahn, Ingold and Prelog. If R is H, the carbon atom denoted by *C is not asymmetric.

In practice, the preferred compounds of formula I containing an asymmetric carbon *C are those in which said carbon has the (R) configuration.

The compounds of formula I can be obtained by methods known per se in which conventional reaction mechanisms are applied, especially reactions which make it possible to obtain groups of the carbamate type.

As indicated above, the method of preparing the compounds of formula I which is recommended according to the invention comprises the deprotection of a compound of formula II. In practice, the group or groups $R_1$ which are to be replaced with hydrogen atoms in the reaction are amino-protecting groups of known type, especially in peptide chemistry, for temporarily blocking "amine" groups which are not totally substituted.

The following may be used among the groups suitable for this purpose:

(a) groups of the oxycarbonyl type, for example alkoxycarbonyl or benzyloxycarbonyl groups:

Boc: t-butoxycarbonyl (or 1,1-dimethylethoxycarbonyl)

Fmoc: 9-fluorenylmethoxycarbonyl

Z: benzyloxycarbonyl (or phenylmethoxycarbonyl)

Z(p-Cl): 4-chlorobenzyloxycarbonyl

Z(p-OMe): 4-methoxybenzyloxycarbonyl (b) groups of the benzyl type, for example the phenylmethyl group (Bn).

Of these amino-protecting groups, the preferred group according to the invention is the group Boc.

The method of preparing a compound of formula I or one of its addition salts comprises the steps which consist in:

(i) deprotecting a compound of the formula

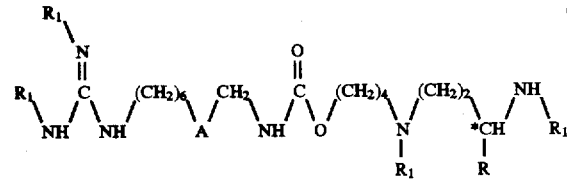

in which:

R is a hydrogen atom or a methyl group,

A is a group —CO—NH— or a group —NH—CO—,

*C, if R is not the hydrogen atom, is an asymmetric carbon of undetermined configuration (R,S) or determined configuration (R), and at least one of the substituents $R_1$ is an amine-protecting group of the oxycarbonyl or benzyl type, the other substituents $R_1$, if appropriate, being a hydrogen atom, by a treatment adapted to the nature of the amino-protecting group, such as, for example, if this amino-protecting group is a group of the alkoxycarbonyl type, by reaction with a strong acid such as trifluoroacetic acid, or if this amino-protecting group is a group of the benzyl type, by catalytic hydrogenation in the presence of a palladium-based catalyst, to give a compound of formula I in the form of the free base or one of its addition salts, and, if necessary, (ii) obtaining the other addition salts from the free base or from its addition salt obtained according to step (i). In step (ii), the conversion of one addition salt to the other addition salts is effected in practice either via the compound of formula I in the form of the free base, or by exchange of the counterion in the presence of an excess of the acid corresponding to the salt to be obtained.

A compound of formula II can be prepared by using a method selected from the following variants:

(a) variant A, which comprises the steps consisting in:

(i) condensing an alcohol of the formula

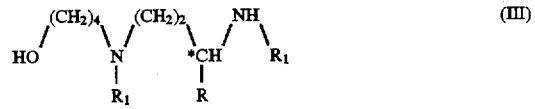

in which:

R is a hydrogen atom or a methyl group, $R_1$ is an amino-protecting group, for example a group Boc, and

*C, if R is not the hydrogen atom, is an asymmetric carbon of (R,S) or (R) configuration, with a chloroformate or a symmetrical carbonate, for example 4-nitrophenyl chloroformate, in the presence of a base, for example triethylamine, in an inert solvent, at room temperature (15°–25° C.), and then (ii) reacting the compound obtained in stage (i) with an amine of the formula

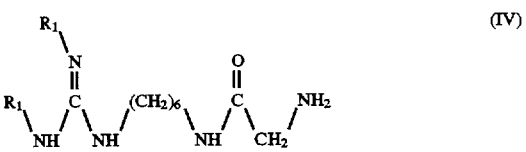

in which $R_1$ is an amino-protecting group, for example a group Boc, in an inert solvent, at a temperature of about 25° to 50° C., to give a compound of the formula

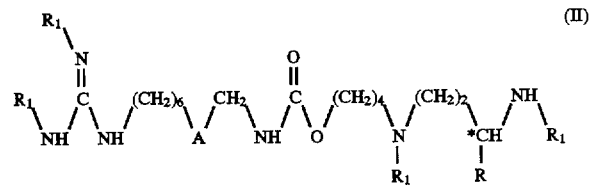

in which:

A is the group —NH—CO—,

R is a hydrogen atom or a methyl group,

*C, if R is not the hydrogen atom, is an asymmetric carbon of (R,S) or (R) configuration, and $R_1$ is an amino-protecting group, for example a group Boc;

and (b) variant B, which comprises the steps consisting in:

(i) reacting an acid of the formula

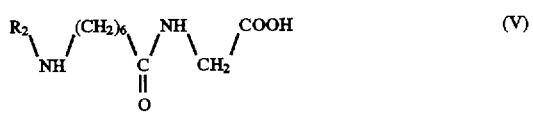

in which $R_2$ is an amino-protecting group, for example a benzyloxycarbonyl group, with diphenylphosphoryl nitride of the formula

in the presence of a base, such as triethylamine in particular, in a solvent, for example tetrahydrofuran, at room temperature, to give an intermediate of the formula

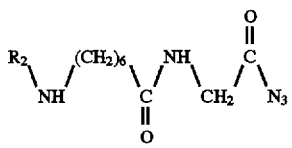
(VII)

(ii) subjecting the compound VII obtained above to a rearrangement known as a Curtius reaction and simultaneously reacting the resulting isocyanate with an alcohol of the formula

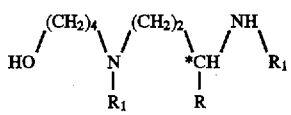
(III)

in which:

R is a hydrogen atom or a methyl group, $R_1$ is an amino-protecting group differing from the group $R_2$ above, for example a group Boc, and

*C, if R is not the hydrogen atom, is an asymmetric carbon of (R,S) or (R) configuration, in a solvent, such as toluene in particular, at a temperature of about 80° to 140° C., for 5 to 50 hours, to give a compound of the formula

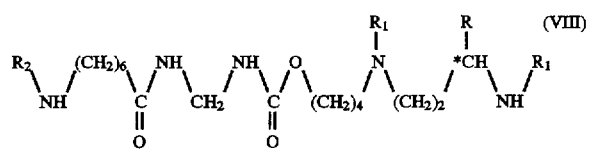
(VIII)

in which R, $R_1$, $R_2$ and *C retain the same definitions as above, (iii) deprotecting the compound VIII obtained above by a treatment specific for the replacement of the amino-protecting group $R_2$ with a hydrogen atom, for example, if $R_2$ is a benzyloxycarbonyl group, by carrying out a catalytic hydrogenation in the presence of a palladium-based catalyst, to give a compound of the formula

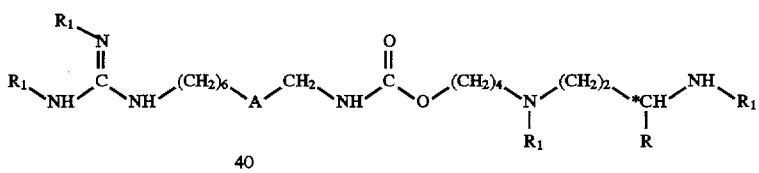
(IX)

in which R, $R_1$ and *C retain the same definitions as above, and (iv) reacting the compound of formula IX obtained in stage (iii) with aminoiminomethanesulfonic acid, in a solvent, for example methanol, at room temperature (15°–25° C.), for 8 to 50 hours, to give a compound of the formula

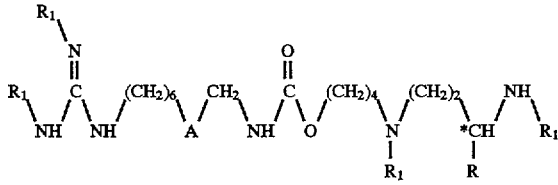
(II)

in which:

R and *C retain the same definitions as above,

A is the group —CO—NH—, and $R_1$ is an amino-protecting group, for example the group Boc, with the exception of the two groups $R_1$ carried by the guanidine group, which are each a hydrogen atom, or (iv') as a variant of step (iv) above, reacting the compound of formula IX with a compound of the formula

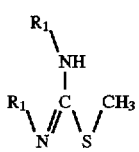
(X)

in which:

$R_1$ is an amino-protecting group, for example a group Boc, in a solvent, for example tetrahydrofuran, in the presence of a base, especially triethylamine, at room temperature, for 8 to 100 hours, to give a compound of the formula

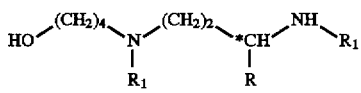
(II)

in which:

A is the group —CO—NH—,

R is a hydrogen atom or a methyl group, $R_1$ is an amino-protecting group, for example a group Boc, and

*C, if R is not the hydrogen atom, is an asymmetric carbon of (R,S) or (R) configuration.

The compound of the formula

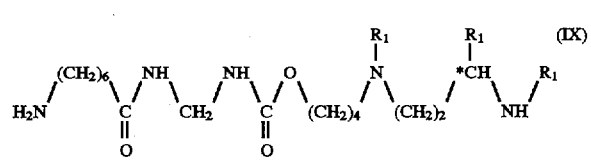
(III)

in which:

R is a methyl group,

*C is a carbon atom of (R,S) or (R) configuration, and $R_1$ is an amino-protecting group, for example a group Boc, can be obtained (a) by reacting 4-aminobutanol with a compound of the formula

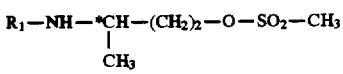

in which $R_1$ is an amino-protecting group, for example the group Boc, to give a compound of the formula

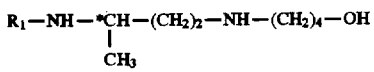

and then introducing an amino-protecting group onto the free amine group, for example with t-butyl dicarbonate ($Boc_2O$) if $R_1$ is the group Boc, to give the expected compound of formula III, or (b) by reacting a halide of the formula

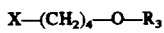

in which X is a halogen, for example an iodine atom or a bromine atom, and $R_3$ is a hydroxyl-protecting group, especially a trityl group, with a compound of the formula

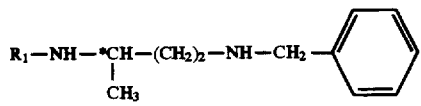

in which $R_1$ is an amino-protecting group, for example the group Boc, to give a compound of the formula

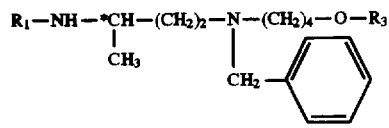

and then selectively deprotecting this product to give the compound of the formula

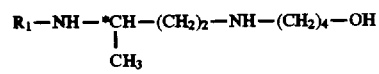

and introducing the amino-protecting group $R_1$ onto this compound, for example by reaction with t-butyl dicarbonate if $R_1$ is the group Boc, to give the expected compound of formula III.

The compounds of formula III in which R is a methyl group and $R_1$ is a group Boc are novel and form one of the subjects of the invention.

The compound of formula V:

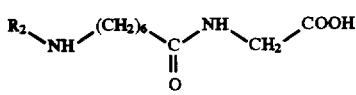

in which $R_2$ is an amino-protecting group, especially the group Z (benzyloxycarbonyl), can be obtained from a compound of the formula

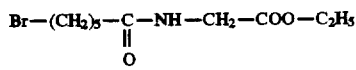

by successive reaction (a) with a cyanide to give the compound of the formula

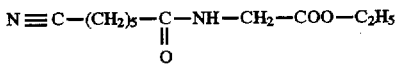

(b) with sodium hydroxide solution to give the acid

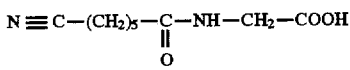

(c) with hydrogen, in the presence of a hydrogenation catalyst, to give the amine

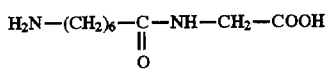

(d) and finally with a reagent for introducing the amino-protecting group, for example benzyl chloroformate, to give the expected compound of formula V in which $R_2$ is a benzyloxycarbonyl group (Z).

The invention will be understood more clearly from the following Examples and the results of pharmacological tests obtained with the compounds according to the invention, by comparison with the results obtained with known products of the prior art. The nomenclature used in the Examples is the one recommended by Chemical Abstracts; thus an ester of the type "t-butyl ... -oate" will be written in the form ". . . -oic acid, 1,1-dimethylethyl ester".

In the experimental section, the Preparations relate to the intermediates and the Examples relate to the products according to the invention.

If the compounds contain an asymmetric carbon in their structure, the absence of any particular notation or the notation (R,S) denotes that they are a substantially equimolecular mixture of the two enantiomers (i.e. the "racemic" compound). If these same compounds are named with the symbol (R) or (S) immediately following the identification of the position of a substituent, this means that the carbon carrying this substituent has the (R) or, respectively, (S) configuration in accordance with the Cahn, Ingold and Prelog rules.

The spectral characteristics of the nuclear magnetic resonance (NMR) signals are given for the proton ($^1H$) or for the 13 isotope of carbon ($^{13}C$) and are indicated as follows: the chemical shift relative to the tetramethylsilane signal and, in brackets, the shape of the signal (s for singlet, d for doublet, t for triplet, q for quadruplet, m for multiplet, bs for broad signal) and the number of protons to which the signal relates. By way of indication, the $^1H$ NMR spectra were run at 300 MHz.

PREPARATION I

3-[[(1,1-Dimethylethoxy)carbonyl]amino]-21-[(1,1-dimethylethoxy)carbonyl]-12,15-dioxo-16-oxa-2,4, 11,14,21,25-hexaazahexacos-2-enedioic acid, bis-(1, 1-dimethylethyl) ester 1 g ($2.89 \cdot 10^{-3}$ mol) of [3-[[(1,1-dimethyl-ethoxy)carbonyl]amino]propyl](4-hydroxybutyl)carbamic acid, 1,1-dimethylethyl ester is dissolved in 20 ml of tetrahydrofuran (THF), and 0.45 g ($4.5 \cdot 10^{-3}$ mol) of triethylamine is added followed by a solution of 0.58 g ($2.89 \cdot 10^{-3}$ mol) of 4-nitrophenyl chloroformate in 5 ml of THF. The reaction mixture is stirred for 15 hours at room temperature, a solution of 1.2 g (2.89·10$^{-3}$ mol) of 13-amino-3-[[(1,1-dimethylethoxy)carbonyl]-amino]-12-oxo-2,4,11-triazatridec-2-enoic acid, 1,1-dimethylethyl ester in 6 ml of THF is then added and the reaction mixture is heated to 40° C. and stirred for 5 hours. After concentration of the reaction medium under reduced pressure, the residue is purified by medium pressure chromatography on silica gel using a methylcyclohexane/ethyl acetate mixture (7/3; v/v) and then pure ethyl acetate as the eluent to give 1 g of the expected product in the form of a transparent oil (yield=44%).

$^1$H NMR (CDCl$_3$): 1.3–1.9 (m, 50H); 3.05–3.55 (m, 10H); 3.85 (d, 2H); 4.10 (t, 2H); 4.7–5.3 (bs, 1H); 5.4–5.6 (bs, 1H); 6.0–6.2 (bs, 1H); 8.3–8.5 (bs, 1H); 11.5 (s, 1H).

Example 1

[4-[(3-Aminopropyl)amino]butoxycarbonylamino]-N-[6-[(aminoiminomethyl)amino]hexyl]acetamide tris(tri-fluoroacetate)

A mixture of 1 g (1.27·10$^{-3}$ mol) of the compound obtained according to Preparation I in 10 ml of dichloromethane and 10 ml of trifluoroacetic acid is prepared and the reaction medium is stirred for 15 hours at room temperature. The solvents are then removed under reduced pressure and the residue is purified by medium pressure chromatography (MPLC) on RP18-type grafted silica (particle size 5 to 20 µm) using an ethanol/water/ trifluoroacetic acid mixture (2/7.5/0.5; v/v) as the eluent. The fractions containing the pure product are concentrated under reduced pressure, redissolved in water and lyophilized to give 0.78 g of the expected product in the form of a translucent white amorphous solid (yield=84%).

$^1$H NMR (DMSO-d$_6$): 1.2–1.55 (m, 8H); 1.6–1.75 (m, 4H); 1.8–1.95 (m, 2H); 2.8–3.1 (m, 10H); 3.55 (d, 2H); 3.95 (t, 2H); 6.7–7.4 (m, 4H); 7.55 (t, 1H); 7.75–8.00 (m, 4H); 8.5–8.65 (m, 3H).

$^{13}$C NMR (D$_2$O/dioxane-h$_8$): 23.05; 24.55; 26.15; 26.20; 26.30; 28.55; 28.95; 31.05; 37.35; 39.95; 41.88; 45.24; 48.18; 65.71; 158.0; 159.0; 178.5.

Example 1bis

[4-[(3-Aminopropyl)amino]butoxycarbonylamino]-N-[6-[(aminoiminomethyl)amino]hexyl]acetamide tris(hydrochloride)

A solution of 3.5 g of the compound of Example 1 (4.8·10$^{-3}$ mol) in 7 ml of anhydrous ethanol is prepared and 10 ml of a 1.3M solution of hydrogen chloride in ethanol are added dropwise at 0° C. Stirring is maintained for 30 minutes after the addition has ended, and the precipitate obtained is then filtered off. After the solid has been washed with anhydrous ethanol, it is dried under vacuum at 35°–40° C. to give the expected product (1.72 g) in the form of a hygroscopic white powder (yield=72%).
M.p.=107.5° C.

PREPARATION II

[3-[[4-[Tris(phenyl)methoxy]butyl](phenylmethyl)amino]-1-(R)-methylpropyl]carbamic acid, 1,1-dimethylethyl ester A solution of 3.77 g (13.5·10$^{-3}$ mol) of [3-(phenylmethylamino)-1-(R)-methylpropyl]carbamic acid, 1,1-dimethylethyl ester in 270 ml of butanol is prepared and 12 g (27.1·10$^{-3}$ mol) of 1-iodo-4-[tris-(phenyl)methoxy] butane and 3.74 g (27.1·10$^{-3}$ mol) of potassium carbonate are then added. The reaction mixture is stirred at 95°–100° C. for 48 hours. After cooling, the reaction medium is filtered and then concentrated under reduced pressure. The residue is then taken up with dichloromethane and washed with water. After concentration of the organic phase under reduced pressure, the product is purified by chromatography on silica gel using a hexane/ethyl acetate mixture (80/20; v/v) as the eluent to give 6 g of the expected product in the form of an oil (yield=75%).

[α]$_D^{24}$=0.22° (c=1.8; CHCl$_3$).

$^1$H NMR (CDCl$_3$): 1.02 (d, 3H); 1.40 (s, 9H); 1.59 (m, 6H); 2.38 (m, 3H); 2.55 (m, 1H); 3.0 (bs, 2H); 3.40 (d, 1H); 3.6 (d, 2H); 5.70 (s, 1H); 7.21–7.43 (m, 20H).

PREPARATION III

[3-[[4-Hydroxybutyl]amino]-1-(R)-methylpropyl]carbamic acid, 1,1-dimethylethyl ester (hydrochloride)

4.94 g (8.33·10$^{-3}$ mol) of the compound obtained according to Preparation II are dissolved in 230 ml of 95° ethanol [i.e. approximately an ethanol/water mixture (95/5; v/v)] and 4.37 ml of a 4.3N solution of HCl in 95° ethanol and 1 g of 5% palladium-on-charcoal are then added. The mixture is then hydrogenated for 40 hours at atmospheric pressure and at room temperature. The catalyst is filtered off and the filtrate is concentrated under reduced pressure. 2.09 g of the expected product are obtained after purification by chromatography on silica gel using a chloroform/methanol mixture (9/1; v/v) as the eluent. After washing with ethyl ether, 1.6 g of pure product are obtained in the form of a white crystalline solid (yield=64.8%).
M.p.=135° C.
[α]$_D^{22}$=–7.6° (c=1; CHCl$_3$).

PREPARATION IV

[3-[(4-Hydroxybutyl)(1,1-dimethylethoxycarbonyl)amino]-1-(R)-methylpropyl]carbamic acid, 1,1-dimethylethyl ester A mixture of 1.54 g (5.18·10$^{-3}$ mol) of the compound obtained according to Preparation III, 8 ml of dioxane and a solution of 0.77 g (7.26·10$^{-3}$ mol) of sodium carbonate in 5.7 ml of water is prepared. This mixture is cooled to 5° C., a solution of 1.13 g (5.18·10$^{-3}$ mol) of ditert-butyl dicarbonate (Boc$_2$O) in 3 ml of dioxane is then added and the reaction mixture is stirred for 15 hours. After the addition of 10 ml of water, extraction is carried out with ethyl acetate and the organic phase is then concentrated under reduced pressure. After purification by chromatography on silica gel using a hexane/ethyl acetate mixture (50/50; v/v) as the eluent, 1.82 g of the expected product are obtained in the form of a colorless viscous oil (yield=97%).

[α]$_D^{22}$=+4.25° (c=2; CHCl$_3$).

$^1$H NMR (CDCl$_3$): 0.87 (d, 3H); 1.44–1.46 (2s, 18H); 1.50–1.70 (m, 6H); 3.20 (m, 4H); 3.67 (t, 3H); 4.41–4.56 (2bs, 1H).

PREPARATION V

[3-[N-[4-[(4-Nitrophenoxy)carbonyloxy]butyl]-N-[1,1-dimethylethoxycarbonyl]amino]-1-(R)-methylpropyl]-carbamic acid, 1,1-dimethylethyl ester A solution of 2.73 g (7.57·10$^{-3}$ mol) of the compound obtained according to Preparation IV in 55 ml of toluene and 0.62 ml (7.7·10⁻³ mol) of pyridine is prepared and 1.6 g (7.7·10⁻³ mol) of 4-nitrophenyl chloroformate are added. The reaction mixture is stirred for 3 hours and the salts formed are then filtered off. The filtrate is concentrated under reduced pressure and then purified by chromatography on silica gel using a dichloromethane/ethyl acetate mixture (90/10; v/v) as the eluent to give 3.1 g of the expected product (yield=78%).

¹H NMR (CDCl₃): 1.15 (d, 3H); 1.44 (s, 9H); 1.46 (s, 9H); 1.5–1.8 (m, 6H); 3.24 (m, 4H); 3.63 (m, 1H); 4.30 (t, 2H); 7.39 (d, 2H); 8.28 (d, 2H).

PREPARATION VI

3-[[(1,1-Dimethylethoxy)carbonyl]amino]-21-[(1,1-dimethylethoxy)carbonyl]-24-(R)-methyl-12,15-dioxo-16-oxa-2,4,11,14,21,25-hexaazahexacos-2-enedioic acid, bis(1,1-dimethylethyl) ester 2.8 g (5.33·10⁻⁵ mol) of the compound of Preparation V are dissolved in 300 ml of THF, and 0.85 ml (6.1·10⁻³ mol) of triethylamine and a solution of 2.54 g (6.1·10⁻³ mol) of 13-amino-3-[[(1,1-dimethyl-ethoxy)carbonyl]amino]-12-oxo-2,4,11-triazatridec-2-enoic acid, 1,1-dimethylethyl ester in 50 ml of THF are then added. The reaction mixture is stirred for 4 hours at room temperature and then concentrated under reduced pressure. The solid residue is purified by chromatography on silica gel using a hexane/ethyl acetate mixture (30/70, then 10/90; v/v) as the eluent to give 3.85 g of the expected product in the form of a light yellow solid (yield=90.2%).

$[\alpha]_D^{20}$=+0.4° (c=2; CHCl₃).
¹H NMR (CDCl₃): 1.15 (d, 3H); 1.3–1.70 (m, 50H); 3.25 (m, 6H); 3.39 (q, 2H); 3.63 (m, 1H); 3.83 (d, 2H); 4.14 (t, 2H); 4.6 (bs, 1H); 5.60 (bs, 1H); 6.13 (bs, 1H); 8.31 (s, 1H); 11.50 (s, 1H).

Example 2

[4-[(3-(R)-Aminobutyl)amino]butoxycarbonylamino]-N-[6-(aminoiminomethylamino)hexyl]acetamide tris (trifluoro-acetate)

3.7 g (4.6·10⁻³ mol) of the compound obtained according to Preparation VI are cooled to 0° C. in a round-bottomed flask and 37 ml of trifluoroacetic acid are added. The mixture is stirred for 15 hours at 5°–10° C. and then concentrated under reduced pressure. The crude product is purified by chromatography on RP18-type grafted silica gel using a water/acetonitrile/trifluoroacetic acid mixture (70/15/15; v/v) as the eluent to give 3.1 g of the expected product in the form of a hygroscopic white solid (yield=92%).

$[\alpha]_D^{24}$=+0.89° (c=2; CH₃OH).
¹H NMR (DMSO-d₆): 1.18 (d, 3H); 1.26 (m, 4H); 1.41 (m, 4H); 1.61 (m, 4H); 1.75 (m, 1H); 1.91 (m, 1H); 2.85–3.20 (m, 8H); 3.28 (m, 1H); 3.54 (d, 2H); 3.96 (bs, 2H); 7.25 (t, 1H); 7.64 (s, 1H); 7.86 (t, 1H); 7.98 (s, 3H); 8.62 (s, 2H).
¹³C NMR (D₂O+dioxane): 17.93; 22.98; 26.06; 26.14; 26.23; 28.49; 28.91; 31.13; 39.89; 41.79; 44.31; 44.52; 46.01; 48.08; 65.60; 157.44; 159.38; 172.64.

Example 2bis

[4-[(3-(R)-Aminobutyl)amino]butoxycarbonylamino]-N-[6-(aminoiminomethylamino)hexyl]acetamide tris (hydrochloride)

A solution of 200 mg (0.27·10⁻³ mol) of the compound obtained in Example 2 in 0.5 ml of ethanol is prepared and 0.235 ml of a 10.4N solution of HCl in ethanol is added. The mixture is stirred for 15 min at room temperature and 2 ml of diisopropyl ether are then added. The precipitated product is separated off by decantation, rinsed with diisopropyl ether and then redissolved in 3 ml of water and lyophilized to give 117 mg of the expected product in the form of an amorphous white solid (yield=85%).

$[\alpha]_D^{22.5}$=+1.45° (c=2; CH₃OH).
¹H NMR (DMSO-d₆): 1.21 (d, 3H); 1.26 (m, 4H); 1.42 (m, 4H); 1.64 (m, 4H); 1.88 (m, 1H); 2.04 (m, 1H); 2.89–3.10 (m, 8H); 3.35–3.70 (m, 3H); 3.97 (bs, 2H); 7.32 (t, 1H); 7.80 (t, 1H); 7.92 (t, 1H); 8.24 (s, 3H); 9.16 (s, 2H).

PREPARATION VII

[3-[N-[4-Hydroxybutyl]amino]-1-(R,S)-methylpropyl]carbamic acid, 1,1-dimethylethyl ester A solution of 6.2 g (23.25·10⁻³ mol) of [1-(R,S)-methyl-3-[(methylsulfonyl)oxy]propyl]carbamic acid, 1,1-dimethylethyl ester in 40 ml of 1,2-di-methoxyethane is prepared and a solution of 4.14 g (46.5·10⁻³ mol) of 4-aminobutanol in 10 ml of 1,2-dimethoxyethane is added dropwise. The reaction mixture is refluxed for 18 hours and then concentrated under reduced pressure. The crude product is purified by chromatography on silica gel using an ethyl acetate/ethanol/33% aqueous ammonia mixture (6/3/0.1; v/v) as the eluent to give 2.5 g of the expected product in the form of an oil (yield=41.5%).

¹H NMR (CDCl₃): 1.14 (d, 3H); 1.44 (s, 9H); 1.5–1.8 (m, 6H); 2.64 (m, 4H); 3.58 (t, 2H); 3.71 (m, 1H); 4.50 (d, 1H).

PREPARATION VIII

[3-[N-(4-Hydroxybutyl)-N-(1,1-dimethylethoxycarbonyl)-amino]-1-(R,S)-methylpropyl]carbamic acid, 1,1-dimethylethyl ester Using a procedure analogous to the method of Preparation IV starting from the compound obtained according to Preparation VII, the expected product is obtained with a yield of 70%.

¹H NMR (CDCl₃): 1.15 (d, 3H); 1.44–1.46 (2s, 18H); 1.5–1.7 (m, 6H); 3.20 (m, 4H); 3.67 (t, 3H); 4.39–4.56 (2bs, 1H).

PREPARATION IX

3-[[(1,1-Dimethylethoxy)carbonyl]amino]-21-[(1,1-dimethylethoxy)carbonyl]-24-(R,S)-methyl-12,15-dioxo-16-oxa-2,4,11,14,21,25-hexaazahexacos-2-enedioic acid, bis(1,1-dimethylethyl) ester 1.8 g (5·10⁻³ mol) of the compound obtained according to Preparation VIII above are dissolved in 36 ml of THF, and 1.1 g (7.8·10⁻³ mol) of triethylamine and 1.10 g (5.45·10⁻³ mol) of 4-nitrophenyl chloroformate are then added. The reaction medium is stirred for 15 hours, a solution of 2.1 g (5.06·10⁻³ mol) of 13-amino-3-[[(1,1-dimethylethoxy)carbonyl]amino]-12-oxo-2,4,11-triazatridec-2-enoic acid, 1,1-dimethylethyl ester in 30 ml of THF is then added and the mixture is stirred for 18 hours. The solid formed by the reaction is filtered off, the solution is then concentrated under reduced pressure and the residue is purified by chromatography on silica gel using a methylcyclohexane/ethyl acetate mixture (50/50, then 20/80; v/v) as the eluent to give 0.97 g of the expected product in the form of an oil (yield=24.2%).

¹H NMR (CDCl₃): 1.15 (d, 3H); 1.20–1.80 (m, 50H); 3.26 (m, 6H); 3.39 (q, 2H); 3.62 (m, 1H); 3.83 (d, 2H); 4.12 (m, 2H); 4.60 (bs, 1H); 5.60 (bs, 1H); 6.13 (bs, 1H); 8.30 (t, 1H); 11.49 (s, 1H).

Example 3

[4-[(3-(R,S)-Aminobutyl)amino]
butoxycarbonylamino]-N-[6-
(aminoiminomethylamino)hexyl]acetamide tris
(trifluoroacetate)

0.95 g (1.18·10⁻³ mol) of the compound obtained according to Preparation IX is dissolved in 10 ml of dichloromethane, and 10 ml of trifluoroacetic acid are then added. After stirring for 24 hours at room temperature, the reaction mixture is concentrated under reduced pressure and the residue is purified by chromatography on RP18-type grafted silica gel using an acetonitrile/water/trifluoroacetic acid mixture (15/80/5; v/v) as the eluent. After lyophilization of the pure fractions, 580 mg of the expected product are obtained in the form of a white solid (yield=66%).

$^1$H NMR (DMSO-$d_6$): 1.18 (d, 3H); 1.26 (m, 4H); 1.41 (m, 4H); 1.61 (m, 4H); 1.74 (m, 1H); 1.91 (m, 1H); 2.85–3.10 (m, 8H); 3.28 (m, 1H); 3.54 (d, 2H); 3.96 (t, 2H); 7.23 (t, 1H); 7.58 (t, 1H); 7.84 (t, 1H); 7.93 (s, 3H); 8.56 (m, 2H). $^{13}$C NMR ($D_2O$+dioxane-$h_a$): 18.02; 23.09; 26.17; 26.22; 26.30; 28.58; 29.00; 31.24; 40.00; 41.88; 44.40; 44.63; 46.10; 48.19; 65.72; 157.55; 159.55; 172.82.

PREPARATION X

N-(6-Cyanohexanoyl)glycine, ethyl ester 23.73 g (84.7·10⁻³ mol) of N-(6-bromohexanoyl)-glycine, ethyl ester are dissolved in 200 ml of ethanol, and 6.5 g (0.1 mol) of powdered potassium cyanide are added. The reaction mixture is brought to the reflux point and stirred under reflux for 15 hours. After concentration of the mixture under reduced pressure, the residue is taken up with dichloromethane and the organic phase is washed with aqueous sodium chloride solution. The organic phase is dried and concentrated under reduced pressure to give 19 g of the expected product (yield=99%).

$^1$H NMR (CDCl$_3$): 1.29 (t, 3H); 1.45–1.55 (m, 2H); 1.6–1.8 (m, 4H); 1.27 (t, 2H); 2.36 (t, 2H); 4.03 (d, 2H); 4.22 (q, 2H); 5.35–6.05 (bs, 1H).

PREPARATION XI

N-(6-Cyanohexanoyl)glycine

A mixture of 19 g (84·10⁻³ mol) of the compound obtained according to Preparation X, 120 ml of 1,2-dimethoxyethane and 120 ml of 1M sodium hydroxide solution is prepared and stirred for 15 min at room temperature. 100 ml of water and 200 ml of dichloromethane are then added and the mixture is acidified to pH 1, with cooling in an ice bath. The aqueous phase is extracted several times with dichloromethane and the combined organic phases are dried and concentrated under reduced pressure to give 10.2 g of the expected product in the form of a straw yellow oil (yield=61%).

$^1$H NMR (CDCl$_3$): 1.45–1.55 (m, 2H); 1.6–1.8 (m, 4H); 2.3 (t, 2H); 2.36 (t, 2H); 4.08 (d, 2H); 6.15–6.25 (bs, 1H).

PREPARATION XII

N-(7-Aminoheptanoyl)glycine (Sodium Salt)

8.2 g (41.4·10⁻³ mol) of N-(6-cyanohexanoyl)-glycine are dissolved in 100 ml of ethanol, and 60 ml of 1M sodium hydroxide solution and 800 mg of Raney nickel are added. The mixture is then stirred under a hydrogen atmosphere, at room temperature and under a pressure of 3.5·10⁵ Pa, for 8 hours. When the reaction has ended, 20 ml of 1M hydrochloric acid are added and the mixture is concentrated under reduced pressure to give 10.2 g of a white pasty solid, which contains the expected salt and sodium chloride and which can be used without further purification in the next step.

$^1$H NMR (DMSO-$d_6$): 1.15–1.6 (m, 8H); 2.08 (t, 2H); 2.56 (t, 2H); 3.32 (d, 2H); 7.1–7.25 (bs, 1H).

PREPARATION XIII

N-[7-[(Phenylmethoxycarbonyl)amino]heptanoyl]
glycine 2 g of the compound obtained according to Preparation XII are dissolved in a mixture of 50 ml of water and 50 ml of ethanol, and 1.06 g (10⁻² mol) of sodium carbonate and then 2.34 g (19.8·10⁻³ mol) of benzyl chloroformate are added. After stirring for 15 hours at room temperature, the reaction medium is brought to pH 1 with 1M hydrochloric acid and then extracted with dichloromethane. The organic phase is dried and concentrated under reduced pressure and the crude product is purified by chromatography on silica gel using an ethyl acetate/ethanol/aqueous ammonia mixture (6/3/0.5; v/v) as the eluent to give 1.3 g of the expected product in the form of a pasty solid.

$^1$H NMR (DMSO-$d_6$): 1.2–1.6 (m, 8H); 2.09 (t, 2H); 2.98 (td, 2H); 3.64 (d, 2H); 5.01 (s, 2H); 7.25 (t, 1H); 7.3–7.4 (m, 5H); 7.94 (t, 1H).

PREPARATION XIV

19-[(1,1-Dimethylethoxy)carbonyl]-9,13-dioxo-14-
oxa-2,10,12,19,23-pentaazatetracosanedioic acid, 1-
(phenyl-methyl) 24-(1,1-dimethylethyl) ester 0.5 g (1.49·10⁻³ mol) of the acid obtained according to Preparation XIII is dissolved in 25 ml of THF, 0.18 g (1.8·10⁻³ mol) of triethylamine is added and the mixture is cooled to 0° C. A solution of 0.46 g (1.67·10⁻³ mol) of diphenylphosphoryl nitride in 5 ml of THF is then added dropwise and the mixture is stirred at room temperature for 45 minutes. The solvent is removed under reduced pressure, the residue is taken up with 2 ml of toluene, and 0.18 g (1.8·10⁻³ mol) of triethylamine and 1.04 g (3·10⁻³ mol) of [3-[[(1,1-dimethylethoxy)carbonyl]amino]propyl](4-hydroxy-butyl)carbamic acid, 1,1-dimethylethyl ester are added. The reaction mixture is refluxed for 20 hours and then concentrated under reduced pressure. The crude product is purified by chromatography on silica gel using a methylcyclohexane/ethyl acetate mixture (gradient of 8/2 to 1/9; v/v) as the eluent to give 0.4 g of the expected product in the form of a white solid (yield=39.6%).

M.p.=115° C.

$^1$H NMR (CDCl$_3$): 1.2–1.7 (m, 32H); 2.15 (t, 2H); 3.05–3.3 (m, 8H); 4.05 (t, 2H); 4.5 (t, 2H); 4.7–4.9 (bs, 1H); 5.08 (s, 2H); 5.7–5.9 (bs, 1H); 6.4–6.6 (bs, 1H); 7.3–7.4 (m, 6H).

PREPARATION XV

22-Amino-6-[(1,1-dimethylethoxy)carbonyl]-12,16-
dioxo-11-oxa-2,6,13,15-tetraazadocosanoic acid, 1,
1-dimethyl-ethyl ester A solution of 0.33 g (0.48·10⁻³ mol) of the compound obtained according to Preparation XIV in 15 ml of ethanol is subjected to catalytic hydrogenation in the presence of 30 mg of 5% palladium-on-charcoal, at atmospheric pressure and at room temperature, for 5 hours. After the catalyst has been filtered off, the solvent is driven off under reduced pressure to give 0.26 g of the expected product in the form of an oil (yield=99%).
$^1$H NMR (CDCl$_3$): 1.2–1.75 (m, 32H); 2.2 (t, 2H); 2.8 (t, 2H); 2.85–3.3 (m, 8H); 4.07 (t, 2H); 4.53 (t, 2H); 4.7–5.4 (bs, 1H); 5.7–6.1 (bs, 1H); 6.4–7.1 (bs, 1H).

PREPARATION XVI

3-[[(1,1-Dimethylethoxy)carbonyl]amino]-21-[(1,1-dimethylethoxy)carbonyl]-11,15-dioxo-16-oxa-2,4,12,14,21,25-hexaazahexacos-2-enedioic acid bis(1,1-dimethylethyl) ester A mixture of 0.26 g (0.477·10$^{-3}$ mol) of the compound obtained according to Preparation XV, 0.276 g (0.95·10$^{-3}$ mol) of [[[(1,1-dimethylethoxy)carbonyl]-amino](methylthio)methylene]carbamic acid, 1,1-dimethylethyl ester and 200 μl of triethylamine in 12 ml of THF is prepared and the reaction medium is stirred for 4 days at room temperature. After evaporation of the solvent under reduced pressure, the crude product is purified by chromatography on silica gel using a methylcyclohexane/ethyl acetate mixture (gradient of 7/3 to 2/8; v/v) as the eluent to give 0.10 g of the expected product in the form of an oil (yield=26.7%).
$^1$H NMR (CDCl$_3$): 1.0–1.8 (m, 50H); 2.16 (t, 2H); 3.05–3.3 (m, 6H); 3.4 (td, 2H); 4.07 (t, 2H); 4.55 (t, 2H); 5.2–5.3 (bs, 1H); 5.7–5.8 (bs, 1H); 6.45–6.55 (bs, 1H); 8.3 (t, 1H); 11.5 (s, 1H).

Example 4

7-[(Aminoiminomethyl)amino]-N-[[4-[(3-aminopropyl)-amino]butoxy]carbonylaminomethyl]heptanamide tris(trifluoroacetate)

Using a procedure analogous to the method of Example 3 starting from the compound obtained according to Preparation XVI, the expected product is obtained with a yield of 54%.
$^1$H NMR (DMSO-d$_6$): 1.2–1.35 (m, 4H); 1.4–1.7 (m, 8H); 1.8–1.95 (m, 2H); 2.06 (t, 2H); 2.8–3.1 (m, 8H); 3.96 (t, 2H); 4.32 (t, 2H); 6.85–7.4 (bs, 3H); 7.55–7.7 (m, 2H): 7.8–8.0 (m, 4H); 8.33 (t, 1H); 8.55–8.7 (m, 2H).

PREPARATION XVII

19-[(1,1-Dimethylethoxy)carbonyl]-22-(R)-methyl-9,13-dioxo-14-oxa-2,10,12,19,23-pentaazatetracosanedioic acid, 1-(phenylmethyl) 24-(1,1-dimethylethyl) ester Using a procedure analogous to the method of Preparation XIV starting from the acid obtained according to Preparation XIII and the alcohol obtained according to Preparation IV, the expected product is obtained in the form of an amorphous solid with a yield of 46%.
$[\alpha]_D^{24}$=–2.2° (c=1.06; CHCl$_3$).
$^1$H NMR (CDCl$_3$): 1.15 (d, 3H); 1.2–1.7 (m, 32H); 2.15 (t, 2H); 3.05–3.35 (m, 6H); 3.55–3.7 (m, 1H); 4.05 (t, 2H); 4.55 (t, 2H); 4.8–4.9 (bs, 1H); 5.09 (s, 2H); 5.1–5.2 (bs, 1H); 5.7–5.9 (bs, 1H); 6.45–6.6 (bs, 1H); 7.3–7.4 (m, 5H).

PREPARATION XVIII

22-Amino-6-[(1,1-dimethylethoxy)carbonyl]-3-(R)-methyl-12,16-dioxo-11-oxa-2,6,13,15-tetraazadocosanoic acid, 1,1-dimethylethyl ester Using a procedure analogous to the method of Preparation XV starting from the compound obtained according to Preparation XVII, the expected product is obtained in the form of an oil with a yield of 99%.
$[\alpha]_D^{20}$=–2.1° (c=1; CHCl$_3$)
$^1$H NMR (CDCl$_3$): 1.15 (d, 3H); 1.2–1.7 (m, 32H); 2.19 (t, 2H); 2.77 (t, 2H); 2.85–3.3 (m, 6H); 3.55–3.7 (m, 1H); 4.07 (t, 2H); 4.52 (t, 2H); 5.7–6.3 (bs, 2H); 6.8–7.0 (bs, 1H).

PREPARATION XIX

22-[(Aminoiminomethyl)amino]-6-[(1,1-dimethylethoxy)-carbonyl]-3-(R)-methyl-12,16-dioxo-11-oxa-2,6,13,15-tetraazadocosanoic acid, 1,1-dimethylethyl ester 0.4 g (0.716·10$^{-3}$ mol) of the compound obtained according to Preparation XVIII is dissolved in 10 ml of methanol, 0.186 g (1.5·10$^{-3}$ mol) of aminoiminomethane-sulfonic acid is added and the reaction mixture is stirred at room temperature for 3 days. After removal of the solvent under reduced pressure, the crude product is purified by chromatography on silica gel using an ethyl acetate/ethanol/aqueous ammonia mixture (6/3/0.1, then 6/3/1; v/v) as the eluent to give 0.37 g of the expected product in the form of an oil (yield=86%).
$[\alpha]_D^{22}$=–1° (c=0.89; CHCl$_3$).
$^1$H NMR (CDCl$_3$): 1.15 (d, 3H); 1.2–1.7 (m, 32H); 2.2 (t, 2H); 2.9–3.3 (m, 6H); 3.5–3.75 (m, 1H); 4.05 (t, 2H); 4.52 (t, 2H); 5.4–5.7 (bs, 2H); 6.3–6.5 (bs, 1H); 7.05–7.3 (bs, 4H); 7.8–8.0 (bs, 1H).

Example 5

7-[(Aminoiminomethyl)amino]-N-[[4-[(3-(R)-aminobutyl)-amino]butoxy]carbonylaminomethyl]heptanamide tris(trifluoroacetate)

Using a procedure analogous to the method of Example 3 starting from the compound obtained according to Preparation XIX, the expected product is obtained in the form of an amorphous solid with a yield of 42%.
$[\alpha]_D^{23}$=+1.2° (c=1; CH$_3$OH).
$^1$H NMR (DMSO-d$_6$): 1.18 (d, 3H); 1.2–1.35 (m, 4H); 1.4–1.55 (m, 4H); 1.55–1.7 (m, 4H); 1.7–1.85 (m, 1H); 1.85–2.0 (m, 1H); 2.05 (t, 2H); 2.85–3.1 (m, 6H); 3.2–3.35 (m, 1H); 3.96 (t, 2H); 4.32 (t, 2H); 6.8–7.5 (bs, 3H); 7.60 (t, 1H); 7.68 (t, 1H); 7.95 (s, 4H); 8.35 (t, 1H); 8.5–8.7 (m, 2H).
$^{13}$C NMR (D$_2$O+dioxane-h$_a$): 18.0; 23.06; 25.79; 26.12; 26.25; 28.45; 28.50; 31.22; 36.27; 41.86; 44.61; 46.08; 46.55; 48.17; 65.48; 157.52; 159.06; 178.36.

The immunosuppressive activity of the products according to the invention was demonstrated by means of a test known as the graft-versus-host reaction. B6D2F1 male mice (C57B1/6×DBA/2 first generation hybrids) are immunosuppressed with an intraperitoneal (i.p.) injection of cyclophosphamide. Three days later (day 0 of the experiment: D$_0$), they receive 4×10$^7$ C57B1/6 mouse splenocytes by intravenous administration. The animals are then divided up into groups of at least 8 and receive a daily treatment from D$_1$ to D$_5$ and from D$_7$ to D$_{10}$ by i.p. administration. The control group receives the vehicle only. The mortality is followed up to D$_{60}$. The results, expressed as the mean survival value in days at the indicated dose, are collated in Table I, in which the values given are significant according to the Logrank test (probability less than or equal to 5%). For comparison, Table I also indicates the values obtained with known products (or products of related structure) of the prior art: (A) 15-deoxyspergualin [in the form of the tris(hydrochloride)] and compound (B), which corresponds to Example 16 of EP-A-0 600 762.

Product B:

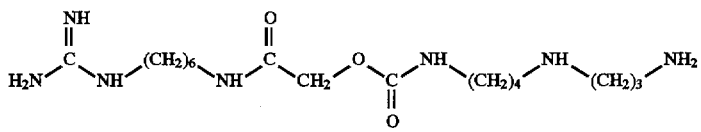

This comparison shows that the products accoring to the invention have a better activity than the products of the prior art or require a lower posology to achieve an equivalent activity.

The products according to the invention are useful in therapeutics as curative or preventive immunosuppressants, especially in preventing the rejection of vascular or non-vascular allogenic or xenogenic organs or the graft-versus-host reaction following a vascularized or non-vascularized graft, in treating genetically defined or acquired autoimmune diseases (for example lupus erythematosus, multiple sclerosis, rheumatoid polyarthritis) or chronic inflammatory diseases, for example articular rheumatism, as well as in any pathological condition where an immune disorder appears to be the cause or factor responsible for maintaining a degraded clinical state.

The products according to the invention can also be administered in combination with cytotoxic anticancer drugs in order to limit their side-effects, and in combination with the administration of products of biotechnological origin, especially recombinant cytokinins or monoclonal and polyclonal antibodies, in order to reduce the appearance of the protective antibodies produced by the patient.

The products according to the invention can be used in the curative treatment of parasitosis, particularly in the case of malaria.

The products according to the invention can be administered orally, by injection (especially intramuscular or intravenous injection), topically (especially in the form of a cream for local application, or eye drops), transdermally, rectally in the form of a suppository, or by inhalation.

The products according to the invention are also useful as pharmacological reagents, especially in the study of autoimmune diseases.

What is claimed is:

1. A compound of the formula

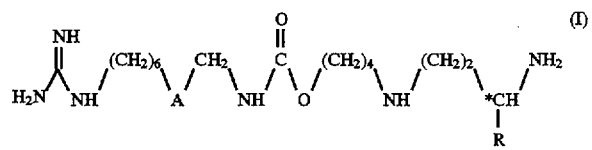

in which:

A is —CO—NH— or —NH—CO—,

R is a hydrogen atom or $CH_3$, and

*C, when and asymmetric carbon is of (R,S) configuration or (R) configuration; or an addition salt thereof.

2. A compound according to claim 1 wherein R is a methyl group and the asymmetric carbon *C has the (R) configuration.

3. A compound according to claim 1 wherein R is hydrogen.

4. A compound according to claim 1 wherein R is a methyl group and the asymmetric carbon *C has the (RS) configuration.

5. A compound according to claim 1, wherein R is a methyl group, A is —NH—CO—, and the asymmetric carbon *C has the (R) configuration.

6. A therapeutic composition which contains, in association with a physiologically acceptable excipient, at least one compound of formula I according to claim 1.

7. A therapeutic composition which contains, in association with a physiologically acceptable excipient, at least one compound of formula I according to claim 2.

8. A therapeutic composition which contains, in association with a physiologically acceptable excipient, at least one compound of formula I according to claim 3.

TABLE I

| Product[a] | A | R | *C | Dose (mg/kg) | Activity (days) |
|---|---|---|---|---|---|
| Ex. 1 | —NH—CO— | H |  | 1 | 53 |
| Ex. 2 | —NH—CO— | $CH_3$ | R | 0.3 | 56 |
| Ex. 3 | —NH—CO— | $CH_3$ | R,S | 1 | 56 |
| Ex. 4 | —CO—NH— | H |  | 0.3 | 45 |
| Ex. 5 | —CO—NH— | $CH_3$ | R | 1 | 58 |
| A (DSG) | for comparison |  |  | 1 | 43 |
| B | for comparison |  |  | 1 | 46 |

Note:
[a]All the tested products of Ex. 1–Ex. 5 according to the invention are in the form of tris(trifluoroacetates).

9. A therapeutic composition which contains, in association with a physiologically acceptable excipient, at least one compound of formula I according to claim 4.

10. In a method of achieving an immunosuppresive effect in a host by administering an immunosuppressive effective amount of a immunosuppressive substance thereto, the improvement which comprises employing a compound of formula I according to claim 1 as said immunosuppressive substance.

11. In a method of achieving an immunosuppresive effect in a host by administering an immunosuppressive effective amount of a immunosuppressive substance thereto, the improvement which comprises employing a compound of formula I according to claim 2 as said immunosuppressive substance.

12. In a method of achieving an immunosuppresive effect in a host by administering an immunosuppressive effective amount of a immunosuppressive substance thereto, the improvement which comprises employing a compound of formula I according to claim 3 as said immunosuppressive substance.

13. In a method of achieving an immunosuppresive effect in a host by administering an immunosuppressive effective amount of a immunosuppressive substance thereto, the improvement which comprises employing a compound of formula I according to claim 4 as said immunosuppressive substance.

14. A method of preparing a compound of formula I according to claim 1, said method comprising the steps of:

(i) deprotecting a compound of the formula

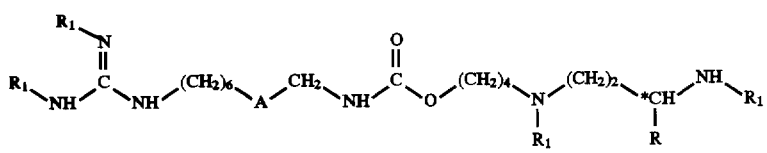

in which:

R is a hydrogen atom or a methyl group,

A is —CO—NH— or —NH—CO—,

*C when as asymmetric carbon is of (R,S) or (R) configuration, and at least one of the substituents $R_1$ is an oxycarbonyl or benzyl amino-protecting group, the other $R_1$ substituents, if different, being a hydrogen atom, to give a compound of formula I in the form of the free base or one of its addition salts, and, if necessary, (ii) obtaining a desired addition salt from the free base or from its addition salt obtained according to step (i).

15. A method according to claim 14 which also comprises steps of:

(a) condensing an alcohol of the formula

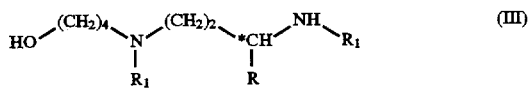

with a chloroformate or a symmetrical carbonate, in the presence of a base, in an inert solvent, at room temperature (15°–25° C.), and reacting the resulting compound obtained with an amine of the formula

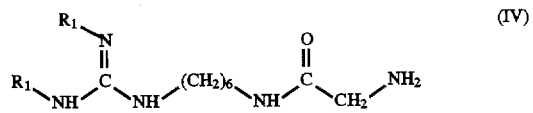

in an inert solvent, at a temperature of about 25° to 50° C., to give a compound of the formula

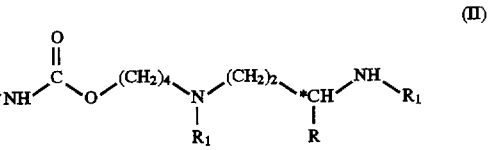

and (b) reacting an acid of the formula

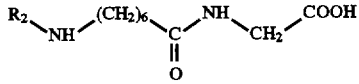

in which $R_2$ is an amino-protecting group, with diphenylphosphoryl nitride of the formula

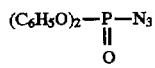

in the presence of a base, in a solvent, at room temperature, to give an intermediate of the formula

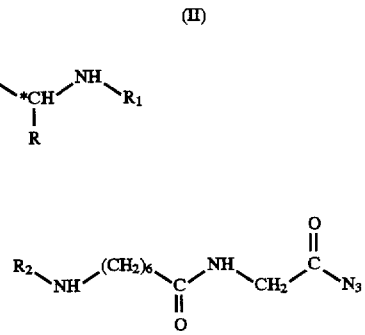

subjecting the compound VII obtained to a Curtius reaction and simultaneously reacting the resulting isocyanate with an alcohol of the formula

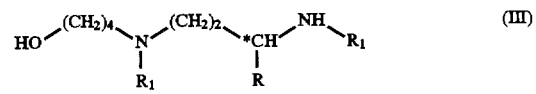

in which:

$R_1$ is an amino-protecting group differing from the group $R_2$ above, in a solvent, at a temperature of about 80° to 140° C., for 5 to 50 hours, to give a compound of the formula

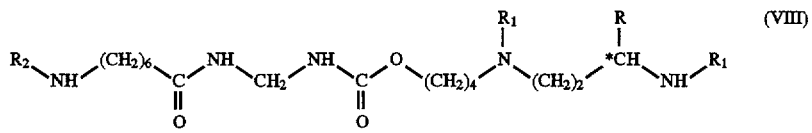

(VIII)

deprotecting the compound VIII obtained by replacement of the amino-protecting group $R_2$ with a hydrogen atom, to give a compound of the formula

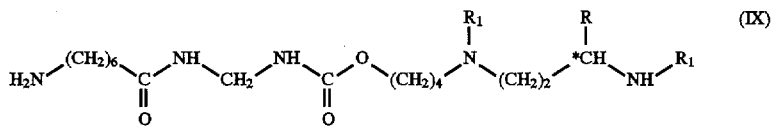

(IX)

and reacting the compound of formula IX obtained stage with aminoiminomethanesulfonic acid, in a solvent, at room temperature (15°–25° C.), for 8 to 50 hours, to give a compound of the formula

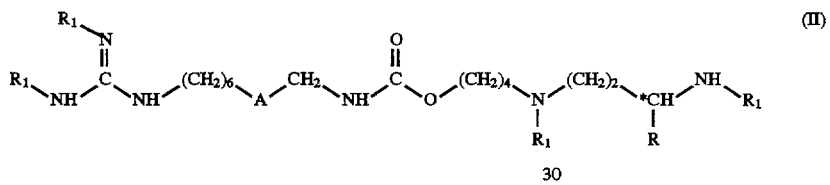

(II)

in which:

A is the group —CO—NH—, and $R_1$ is an amino-protecting group, with the exception of the two groups $R_1$ carried by the guanidine group, which are each a hydrogen atom, or reacting the compound of formula IX with a compound of the formula

(X)

in which:

$R_1$ is an amino-protecting group, in an inert solvent, in the presence of a base, at room temperature (15°–25° C.), for 8 to 100 hours, to give a compound of the formula

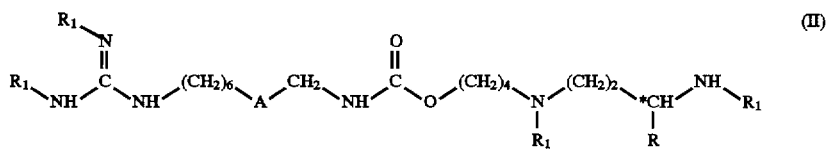

(II)

\* \* \* \* \*